United States Patent [19]

Myers

[11] 4,428,935
[45] Jan. 31, 1984

[54] PENICILLANIC ACID DIOXIDE PRODRUG

[75] Inventor: Robert F. Myers, East Lyme, Conn.

[73] Assignee: Pfizer Inc., New York, N.Y.

[21] Appl. No.: 381,104

[22] Filed: May 24, 1982

[51] Int. Cl.$^3$ ............... C07D 499/00; C07D 499/32; A61K 31/425
[52] U.S. Cl. ........................ 424/114; 260/245.2 R; 424/270
[58] Field of Search ............ 260/245.2 R, 245.2 T; 424/270, 271, 114

[56] References Cited

U.S. PATENT DOCUMENTS

| | | | |
|---|---|---|---|
| 4,234,579 | 11/1980 | Barth | 424/246 |
| 4,244,951 | 1/1981 | Bingham | 424/250 |
| 4,276,285 | 6/1981 | Barth | 424/114 |
| 4,323,499 | 4/1982 | Myers | 260/239.1 |

OTHER PUBLICATIONS

C. Kaiser and J. Winstock, "Alkenes via Hofmann Elimination; Use of Ion-Exchange Resin for Preparation of Quaternary Amines . . . " *Organic Synthesis*, vol. 55, pp. 3–7, (1976).

H. Ferres, "Prodrugs of B-Lactam Antibiotics," *Chemistry and Industry*, 1980, pp. 435–440.

N. Bodor, et al., "Soft Drugs. I. Labile Quaternary Ammonium Salts as Soft Antimicrobials," *J. Medicinal Chem.*, vol. 23, pp. 469–480, (1980).

N. Bodor, et al., "Soft Drugs. II. Soft Alkylating Agents as Potential Antitumor Agents," *J. Medicinal Chem.*, vol. 23, pp. 566–569, (1980).

*Primary Examiner*—Nicholas S. Rizzo
*Attorney, Agent, or Firm*—Charles J. Knuth; Peter C. Richardson; Allen Bloom

[57] ABSTRACT

A compound of the formula

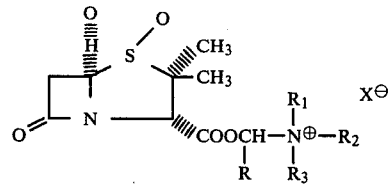

is a prodrug of 4,4-dioxopenicillanic acid, wherein R is hydrogen or methyl; $R_1$, $R_2$ and $R_3$ (a) when taken individually are each alkyl containing one to four carbon atoms, or (b) when taken together with the nitrogen to which they are attached form a five- or six-membered saturated monocyclic moiety, an eight-membered saturated bicyclic moiety or a five- or six-membered aromatic cyclic moiety annulated with zero, one or two fused benzene rings, with the proviso that any $R_1$, $R_2$ or $R_3$ not part of a cyclic moiety is alkyl containing one to four carbon atoms; and $X^-$ is a pharmaceutically-acceptable anion. The prodrug can be included with a beta-lactam antibiotic in a pharmaceutical composition which can be employed in the treatment of infection in mammals. The above-described compounds hydrolyze in vivo to 4,4-dioxopenicillanic acid.

13 Claims, No Drawings

PENICILLANIC ACID DIOXIDE PRODRUG

This invention relates to methyl ammonium derivatives of 4,4-dioxopenicillanic acid which are prodrugs of the parent compound. The invention can be employed with beta-lactam antibiotics for the treatment of infections in mammals.

BACKGROUND OF THE INVENTION

Beta-lactam antibiotics, which generally are penicillins and cephalosporins, have been widely used in the treatment of infections, primarily bacterial, in mammals such as man. Certain micro-organisms are believed to be resistant to these antibiotics because they produce an enzyme, beta-lactamase, which attacks the beta-lactam ring of the antibiotic thereby rendering the drug ineffective.

Barth, in U.S. Pat. No. 4,234,579, has disclosed that 4,4-dioxopenicillanic acid (penicillanic acid 1,1-dioxide) and esters thereof which are readily hydrolyzable in vivo, have antibacterial activity and inhibit microbial beta-lactamases. Barth's inhibitors can be combined with beta-lactam antibiotics to obtain compositions of enhanced effectiveness against microorganisms normally resistant to treatment with the antibiotic alone.

The ester derivatives of 4,4-dioxopenicillanic acid are normally insoluble in aqueous solutions. In some instances, particularly for oral administration, it would be desirable to have a prodrug of 4,4-dioxopenicillanic acid which is water soluble.

SUMMARY OF THE INVENTION

The present invention comprises derivatives of penicillanic acid dioxide having improved water solubility of the formula

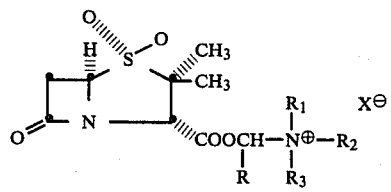

which are prodrugs of 4,4-dioxopenicillanic acid, wherein R is hydrogen or methyl; $R_1$, $R_2$ and $R_3$ (a) when taken individually are each alkyl containing one to four carbon atoms, or (b) when taken together with the nitrogen to which they are attached form a five- to six-membered saturated monocyclic moiety, an eight-membered saturated bicyclic moiety or a five- or six-membered aromatic cyclic moiety annulated with zero, one or two fused benzene rings, with the proviso that any $R_1$, $R_2$, or $R_3$ not part of a cyclic moiety is alkyl containing one to four carbon atoms; and $X^-$ is a pharmaceutically-acceptable anion.

These derivatives can be included with beta-lactam antibiotics in pharmaceutical compositions which can be employed in the treatment of infections in mammals. The above-described derivatives hydrolyze in vivo to 4,4-dioxopenicillanic acid. The cyclic moieties include morpholine, piperidine, 4-aminocarbonylpiperidine, pyrrolidine, 4-methylpyridine, 4-t-butylpyridine, 4-cyanopyridine, 4-N,N-dimethylaminopyridine, 4-acetylpyridine, isonicotinamide, methyl isonicotinate, 3-chloropyridine, 3-acetylpyridine, nicotinamide, methyl nicotinate, 3,5-lutidine, 2,4,6-trimethylpyridine, 1-methylimidazole, bicyclo[2.2.2]-1,4-diazoctane, pyridine and quinoline.

DETAILED DESCRIPTION

A convenient starting material for the synthesis of (1) is 4,4-dioxopenicillanic acid (2,$R_4$=H), which

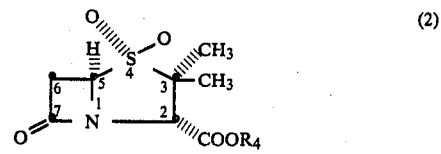

can be synthesized according to the procedures of Barth in the aforementioned U.S. Pat. No. 4,234,579. The numbering of the ring positions is as shown. The acid (2,$R_4$=H) as its salt, e.g., with alkali metal ions such as potassium and sodium or ammonium ions, preferably tetra-n-butylammonium, is readily converted to its chloromethyl or chloroethyl ester (2,$R_4$=CH(R)Cl, wherein R=H or $CH_3$). The chloro ester (2,$R_4$=CH(R)Cl) can be reacted with an iodide salt, preferably sodium iodide, in a non-nucleophilic aprotic solvent, preferably acetone, at a temperature of between about 0° and 50° C., preferably 20°–30° C., to obtain the iodo ester (2,$R_4$=CH(R)I). Either the iodo ester (2,$R_4$=CH(R)I) or the chloro ester (2,$R_4$=CH(R)Cl) is in turn reacted with a nitrogen compound of the formula

wherein $R_1$, $R_2$ and $R_3$ are as previously described for (1) at a temperature between about 0°–50° C., preferably 20°–30° C., in an aprotic, non-nucleophilic solvent such as tetrahydrofuran, acetonitrile, 1,4-dioxane and chloroform to obtain a compound of the present invention (1, $X^-$ = $I^-$ or $Cl^-$, respectively).

In the ester derivatives for reaction with (3) the leaving group (Y), i.e. (2, $R_4$=CH(R)Y), which is displaced by (3) need not be iodo or chloro but may be any suitable leaving group such as bromo, alkyl-sulfonyloxy having one to four carbon atoms, benzenesulfonyloxy, toluensulfonyloxy and the like. Compounds which may be reacted with the acid (2, $R_4$=H) salt to yield (2, $R_4$=CH(R)Y) have the general formula $CHRY_1Y_2$, wherein $Y_1$ and $Y_2$ are each leaving groups, and include bromoiodomethane, chloroiodomethane, diiodomethane, di(methylsulfonyloxy)methane, di(isobutylsulfonyloxy)methane, di-(benzenesulfonyloxy)-methane, di(4-toluenesulfonyloxy)methane, 1,1-diiodoethane and 1,1-dibromoethane. A suitable solvent for these substitution reactions when the reagent itself does not act as the solvent is a non-nucleophilic, aprotic solvent such as tetrahydrofuran, dichloromethane, dimethylformamide, chloroform, 1,4-dioxane and the like. The reaction is generally run between about 0° and 50° C., preferably 20°–30° C.

If Y is the desired counter ion in (1), that is, $Y^-$ = $X^-$, then no further reaction is needed. Otherwise $Y^-$ can be replaced by $X^-$ using conventional techniques. For example, if Y is bromo, chloro or iodo, an aqueous solution of the halide (1,$X^-$ = $Br^-$,$Cl^-$, or $I^-$) can be treated with an equivalent of silver oxide, followed by separation of the precipitated silver halide and treatment of the aqueous solution of the resulting base (1,X$^-$=OH) with at least an equivalent of an appropriate acid HX.

Alternatively, the base (1,X$^-$=OH) can be obtained by passing a solution of (1) through a basic ion-exchange resin column to substitute hydroxyl for X$^-$ followed by treatment of the eluant with the appropriate acid. See C. Kaiser and J. Winstock, Organic Synthesis, volume 55, pages 3–7 (1976). Suitable pharmaceutically acceptable anions include chloride, bromide, iodide, nitrate, acetate, gluconate, benzoate, propionate, butyrate, laurate, stearate, 3-hydroxy-2-naphthoate, p-toluenesulfonate, methanesulfonate, lactate and the like.

A number of amines (3) may be employed in the substitution reaction. The amine (3) selected should be such that the resulting compound (1) is hydrolyzable in vivo to yield 4,4-dioxopenicillanic acid (2, R$_4$=hydrogen) as well as other hydrolysis products which are pharmaceutically acceptable. The physiological pH is about 7.4 under in vivo conditions. For oral ingestion by mammals, the pH encountered in the gastrointestinal system can be considerably more acidic. In addition, the amine (3) chosen should result in a compound (1) which is pharmaceutically acceptable. It will be appreciated that large number of amines (3) from a variety of structural classes may be employed if they have the desired properties. Of course, amines (3) can be chosen to form a compound (1), not having the needed pharmaceutical and hydrolysis properties, which can undergo transformations which result in another compound (1) having the needed pharmaceutical and hydrolysis properties.

Suitable acyclic alkyl amines, preferably with $R_1$, $R_2$ and $R_3$ being $C_{1-4}$ alkyls, include triethylamine and dimethyl-n-propylamine. $R_1$, $R_2$ and $R_3$ alkyl groups can also be substituted with hydroxyl, alkoxycarbonyl wherein the alkoxy has 1–4 carbon atoms, aminocarbonyl and the like.

Saturated cyclic amines can also be employed. Any of $R_1$, $R_2$ and $R_3$ not in the cyclic moiety are alkyl having one to four carbon atoms. Preferred saturated monocyclic amines are five- or six-membered rings such as 1-methylmorpholine, 1-methylpiperidine, 1-methylpyrrolidine and include rings substituted with $C_{1-4}$ alkyl, aminocarbonyl, hydroxyl, alkoxycarbonyl wherein the alkoxy has 1–4 carbon atoms, and the like, such as 1-methyl-4-aminocarbonylpiperidine (N-methylisonipecotamide). Preferred saturated bicyclic amines have eight membered rings such as bicyclo [2.2.2]-1,4-diazaoctane.

Aromatic cyclic amines which are useful include five- and six-membered rings annulated with zero, one or two benzene rings such as pyridine, quinoline, imidazole, thiazole, indole, pyrrole, oxazole, pyrazole, pyrimidine, purine, carbazole and the like, and include those having substituents such as one or more, preferably one-three, of halo (F,Cl,Br, I), alkyl having 1–4 carbon atoms, cyano, alkoxycarbonyl wherein the alkoxy has 1–4 carbon atoms, alkylcarbonyl wherein the alkyl has 1–4 carbon atoms, N,N-dialkylamino wherein each alkyl has 1–4 carbon atoms, aminocarbonyl including N-alkyl and N,N-dialkyl aminocarbonyl, with each alkyl being $C_{1-4}$, can also be employed. Examples of substituted aromatic cyclic amines include 4-methylpyridine, 4-t-butylpyridine, 4-cyanopyridine, 4-N,N-dimethylaminopyridine, methyl isonicotinate, 4-acetylpyridine, isonicotinamide, 3-chloropyridine, 3-acetylpyridine, methyl nicotinate, nicotinamide, 3,5-lutidine, dimethyl 3,5-pyridinedicarboxylate, 2,4,6-trimethylpyridine, and 1-methyl-3-imidazole Compounds of the formula (1) are readily hydrolyzable in vivo in mammals. The resulting penicillanic acid dioxide is an antibiotic and also a beta-lactamase inhibitor which increases the effectiveness of other beta-lactam antibiotics against beta-lactamase-producing bacteria.

The ability of compounds (1) of the present invention to enhance the effectiveness of a beta-lactam antibiotic against beta-lactamase producing bacteria makes these compounds valuable for coadministration with beta-lactam antibiotics in the treatment of bacterial infection in mammals, including man. In the treatment of a bacterial infection, a compound (1) of the present invention can be combined or mixed with the beta-lactam antibiotic and the two agents thereby administered simultaneously. Alternatively, the compound (1) can be administered as a separate agent during a course of treatment with a beta-lactam antibiotic. In some instances it will be advantageous to pre-dose the subject with the compound (1) before initiating treatment with a beta-lactam antibiotic.

When the compound (1) is employed to enhance the effectiveness of a beta-lactam antibiotic, it is administered preferably in formulation with a pharmaceutically acceptable carrier or diluent. The improved water solubility of (1) can lead to greater flexibility in the formulation. The formulation can be administered orally or parenterally, i.e. intramuscularly, subcutaneously, intraveneously or intraperitoneally. The carrier or diluent is chosen on the basis of the intended mode of administration. For example, when considering the oral mode of administration, an antibacterial formulation of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredients, as well as the dosage contemplated. However, pharmaceutical compositions containing a beta-lactam antibiotic and a compound (1) of the present invention will preferably contain from about 20% to about 95% of active ingredients. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous solutions or suspensions are required for oral use, the active ingredient may be combined with emulsifying and suspending agents. The increased water solubility of the compound (1) of the present invention can eliminate or decrease the need for such emulsifying and suspending agents. If desired, certain sweetening and/or flavoring agents can be added. For parenteral administration, sterile solutions of the active ingredients are usually prepared, and the pH of the solutions is suitably adjusted and buffered. For intravenous use, the total concentration of solutes should be controlled to render the preparation isotonic.

When using compounds (1) of the present invention in vivo in combination with another beta-lactam antibiotic, the compound (1) can be administered orally or parenterally. Although the prescribing physician will ultimately decide the dosage to be used in a human subject, the dosage ratio of the penicillanic acid dioxide prodrug (1) and the beta-lactam antibiotic will normally be in the range from about 1:3 to 3:1 by weight. Additionally, when using the pencillanic acid dioxide prodrug (1) in combination with another beta-lactam antibiotic, the daily oral dosage of each component will normally be in the range from about 10 to about 200 mg. per kilogram of body weight and the daily parenteral dosage of each component will normally be about 10 to about 400 mg. per kilogram of body weight. These figures are illustrative only, however, and in some cases it may be necessary to use dosages outside these limits. The same considerations in administering penicillanic acid dioxide prodrugs (1) in combination with a beta-lactam antibiotic apply when the prodrug (1) is administered without another beta-lactam antibiotic.

Typical beta-lactam antibiotics with which the penicillanic acid dioxide prodrug (1) can be co-administered are:

6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)penicillanic acid,
6-(D-2-amino-2-[1,4-cyclohexadienyl]acetamido)-penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-[3-methylsulfonylimidazolidin-2-one-1-carboxamido]-2-phenylacetamido)penicillanic acid,
6-([hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]-acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]-acetamido)penicillanate,
1-(ethoxycarbonyloxy)ethyl 6-(2-phenylacetamido)-penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)-penicillanate,
3-phthalidyl 6-(D-2-amino-2-[4-hydroxyphenyl]-acetamido)penicillanate,
6-(2-phenoxycarbonyl-2-phenylacetamido)penicillanic acid,
6-(2-tolyoxycarbonyl-2-phenylacetamido)penicillanic acid,
6-(2-[5-indanyloxycarbonyl]-2-phenylacetamido)-penicillanic acid,
6-(2-phenoxycarbonyl-2-[3-thienyl]acetamido)-penicillanic acid,
6-(2-tolyloxycarbonyl-2-[3-thienyl]acetamido)penicillanic acid,
6-(2-[5-indanyloxycarbonyl]-2-[3-thienyl]acetamido)-penicillanic acid,
6-(2,2-dimethyl-5-oxo-4-phenyl-1-imidazolidinyl)-penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-amino-2-phenylacetamido)-3-desacetoxycephalosporanic acid,
7-(D-2-phenylglycinamido)-3-chloro-3-desacetoxymethylcephalosporanic acid,
7-(D-2-[4-ethylpiperazin-2,3-dione-1-carboxamido]-2-[4-hydroxyphenyl]-acetamido)-3-([1-methyl-5-tetrazolyl]thiomethyl)-3-desacetoxymethylcephalosporanic acid,
7-(2-cyanoacetamido)cephalosporanic acid,
7-(2-[4-pyridylthio]acetamido)cephalosporanic acid,
7-(D-2-hydroxy-2-phenylacetamido)-3-([1-methyl-5-tetrazolyl]thiomethyl)-3-desacetoxymethylcephalosporanic acid,
7-(D-2-amino-2-[1,4-cyclohexadienyl]acetamido)cephalosporanic acid, or
7-(D-2-amino-2-phenylacetamido)cephalosporanic acid, and the pharmaceutically acceptable salts thereof.

As will be appreciated by one skilled in the art, some of the above beta-lactam compounds are effective when administered orally or parenterally, while others are effective only when administered by the parenteral route. When the penicillanic acid dioxide prodrug (1) is to be combined with a beta-lactam antibiotic which is effective only on parenteral administration, a combination formulation suitable for parenteral use will be employed. When the penicillanic acid dioxide prodrug (1) is to be combined with a beta-lactam antibiotic which is effective orally or parenterally, combinations suitable for either oral or parenteral administration can be prepared. Additionally, it is possible to administer preparations of the penicillanic acid dioxide prodrug (1) orally, while at the same time administering a further beta-lactam antibiotic parenterally; and it is also possible to administer preparations of the penicillanic acid dioxide prodrug (1) parenterally, while at the same time administering the further beta-lactam antibiotic orally.

The pharmokinetics of the compounds (1) of the present invention can be determined using out-bred Sprague-Dawley rats available from commercial suppliers. The rats employed preferably weigh between about 80-100 grams. The dosages are calculated in terms of milligrams of compound (1) per kilogram of weight of the rat. The prodrug (1) to be evaluated or the control can be solubilized or suspended in a suitable diluent. The common dosage can be adjusted so that 10 mg/kg. of 4,4-dioxopenicillanic acid would be available to the animal upon complete hydrolysis of the prodrug or control so that different materials can be evaluated. For oral administration, a convenient volume is 0.5 ml. The controls which are employed are 4,4-dioxopenicillanic acid and a readily-hydrolyzable ester thereof such as the pivaloyloxymethyl ester, described by Barth, U.S. Pat. No. 4,234,579, which was not soluble in an aqueous diluent.

In all cases blood serum is taken from the rat in the following times following oral administration: 0.25, 0.5, 1.0, 1.5, 2.0, 3.0 and 4.0 hours. A bioassay for 4,4-dioxopenicillanic acid is then performed on the serum. Sterile filter paper discs are loaded with 25 lambda volumes of the blood serum. To 100 ml of Mueller-Hinton agar that had been treated with 50 micro g/ml of ampicillin and 5% sterile bovine blood serum filtrate is added 1 ml of an overnight culture of *Pasteurella histolytica* (59B010). *Pasteurella histolytica* is insensitive to high concentrations of either ampicillin or 4,4-dioxopenicillanic acid. However, since its resistance to ampicillin is mediated by a beta-lactamase the culture responds synergistically to combinations of ampicillin and 4,4-dioxopenicillanic acid.

The results are compared using standard curves. The concentrations of 4,4-dioxopenicillanic acid are usually 4, 2, 1, 0.5, 0.25 and 0.125 micro g/ml. As with the test samples, the sterile filter paper discs are loaded with 25 lambda volumes of bovine blood serum at each concentration.

The present invention will be further illustrated by means of the following examples. It is to be understood, however, that the invention is not meant to be limited to the details described therein.

Infrared (IR) spectra were measured as potassium bromide discs (KBr discs), and diagnostic absorption bands are reported in wave numbers (cm$^{-1}$). Nuclear magnetic resonance spectra (NMR) were measured at 60 MHz for solutions in deuterochloroform (CDCl$_3$) or perdeuterodimethylsulfoxide (DMSO-d$_6$) alone or with deuterium oxide (D$_2$O), and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quarter; m, multiplet; b, broad.

EXAMPLE 1

1-(4',4'-Dioxo-penicillanoyloxymethyl)-3,5-dimethyl-pyridinium Iodide

To a solution of 1.0 g. (2.68 mmole) of iodomethyl 4,4-dioxopenicillanate in 5 ml. of tetrahydrofuran, 0.28 g. (2.6 mmole) of 3,5-lutidine was added while stirring at 25° C. After 1 hour, a solid precipitated was filtered, washed with tetrahydrofuran and dried in vacuo to give 0.98 g. of a white crystalline solid of the titled product (yield ca. 76%), m.p. 184°-85° C.(d). The IR spectrum of the product (KBr disc) showed absorptions at 1786 and 1795 cm$^{-1}$. The NMR spectrum (DMSO-d$_6$) showed absorptions at 1.4 (s, 3H), 1.5 (s,3H), 2.63 (s, 6H), 3.1-3.9 (m, 2H), 4.6 (s, 1H), 5.1-5.3 (m, 1H), 6.4-6.8 (m, 2H), 8.5 (s,1H), and 9.1 (s, 2H) ppm.

EXAMPLE 2

The procedure of Example 1 was repeated with the same starting materials except that amines other than 3,5-lutidine were employed to obtain the corresponding 4,4-dioxopenicillanate as tabulated in Table 1. In the case of N-methylisonipecotamide (1-methyl-4-carbamoylpiperidine), the reaction is heterogeneous throughout, as opposed to the solution of Example 1.

TABLE 1

| Amine | Product |
|---|---|
| methylmorpholine | 1-(4',4'-dioxo-penicillanoyloxomethyl)-1-methylmorpholinium iodide (52% yield, IR: 1788 cm$^{-1}$, NMR (DMSO-d$_6$): 1.43 (s,3H), 1.53 (s,3H), 3.27 (s,3H, 3.0-3.7 (bs,6H), 4.0 (bs,4H), 5.0 (s,1H), 5.16 (d of d, 1H, J = 2), 5.3-5.8 (d of d, J-2 and 8, 2H) ppm) |
| methylpiperidine | 1-(4',4'-dioxo-penicillanoyloxymethyl)-1-methylpiperidinium iodide (m.p. 197.5-198° C., 85% yield, IR: 1792 cm$^{-1}$, NMR(DMSO-d$_6$): 1.4(s,3H), 1.5(s,3H,) 1.62-2.1 (bs,6H), 3.0-3.9 (m,9H[3.10(s,3H]), 5.0 (s,1H), 5.1-5.3 (m,1H), 5.3-5.7(m,2H) ppm) |
| methylpyrrolidine | 1-(4',4'-dioxo-penicillanoyloxymethyl)-1-methylpyrrolidinium iodide (m.p. 178.5-179° C. (d), 89% yield, IR: 1782 cm$^{-1}$, NMR(DMSO-d$_6$): 1.4(s,3H), 1.5 (s,3H), 2.0-2.4 (bs,4H), 3.0-4.0 (bm, 9H (s at 3.2)), 4.9(s,1H), 5.1-5.3 (m,1H), 5.4-5.7 (m,2H) ppm) |
| isonicotinamide | 1-(4',4'-dioxo-penicillanoyloxymethyl)-isonicotinamidium iodide (m.p. 189-190° C. (d), 44% yield, IR: 1787, 1689 cm$^{-1}$, NMR (DMSO-d$_6$) 1.4 (s,3H), 1.5 (s,3H), 3.1-3.9(m,2H), 4.6 (s,1H), 5.1-5.3(m,1H), 6.6-6.8 (m,2H), 8.5-8.7 (d, J = 6, 2H), 9.4-9.6 (d,J = 6, 2H) ppm) |
| 3-chloropyridine | 1-(4',4'-dioxo-penicillanoyloxymethyl)-3-chloropyridinium iodide (m.p. 129-130° C.(d), 38% yield, IR: 1790, 1779, NMR (DMSO-d$_6$): 1.4(s,3H), 1.5 (s,3H), 3.1-3.9 (m,2H), 4.6 (s,1H), 5.1-5.3 (m,1H,), 6.4-6.8 (m,2H), 8.1-8.4 (d of d, J = 6 and 7,1H), 8.8-9.0 (d,J = 7,1H), 9.2-9.4 (d,J = 6,1H), 9.7 (s,1H) ppm) |
| quinoline | 1-(4',4'-dioxo-penicillanoyloxymethyl)-quinolinium iodide (m.p. 145-48° C.(d), 30% yield, IR: 1790, 1769 cm$^{-1}$, NMR (DMSO-d$_6$): 1.4 (s,3H), 1.5 (s,3H), 3.1-3.9(m,2H, 4.5(s,1H), 5.1-5.3(m,1H), 7.0(s,2H), 8.0-9.3(m,7H) ppm) |
| 4-t-butylpyridine | 1-(4',4'-dioxo-penicillanoyloxymethyl)-4-t-butylpyridinium iodide (m.p. 183-84° C.(d), 68% yield, IR: 1800, 1768 cm$^{-1}$, NMR (DMSO-d$_6$): 1.4 (s,12H), 1.5 (s,3H), 3.1-3.9(m,2H), 4.5(s,1H), 5.1-5.3(m,1H), 6.4 (s,2H), 8.2-8.4(d,J = 6,2H), 9.0-9.2(d,J = 6,2H) ppm) |
| pyridine | 1-(4',4'-dioxo-penicillanoyloxymethyl)-pyridinium iodide (m.p. 186° C.(d), 51% yield, IR: 1789, 1751 cm$^{-1}$, NMR (DMSO-d$_6$): 1.4 (s,3H), 1.5(s,3H), 3.1-3.9(m,2H), 4.6(s,1H), 5.1-5.3(m,1H), 6.7(s,2H), 8.0-9.0(m,5H) ppm) |
| 4-methylpyridine | 1-(4',4'-dioxo-penicillanoyloxymethyl)-4-methylpyridinium iodide (m.p. 120° C.(d), 66% yield, IR: 1790, 1759 cm$^{-1}$, NMR (DMSO-d$_6$/D$_2$O): 1.4(s,3H), 1.6 (s,3H). 2.75 (s,3H), 3.4-3.8(m,2H), 4.7(s,1H), 5.0-5.2(m,1H), 6.3-6.6(m,2H), 7.9-8.1(d,J = 6,2H), 8.8-9.0(d,J = 6,2H) ppm) |
| nicotinamide | 1-(4',4'-dioxo-pencillanoyloxymethyl)-nicotinamidium iodide (76% yield, IR: 1795, 1789, 1691 cm$^{-1}$, NMR (DMSO-d$_6$): 1.4 (3H), |

TABLE 1-continued

| Amine | Product |
|---|---|
| | 1.5 (s,3H), 3.1–3.9 (m,2H), 4.6 (s,1H), 5.1–5.3 (m,1H), 6.5–6.9 (m,2H), and 8.0–9.6 (m,4H) ppm). |
| 1-methyl-4-amino-carbonylpiperidine | 1-(4',4'-dioxo-penicillanoyloxymethyl)-1-methyl-4-aminocarbonylpiperidinium iodide (93% yield, IR: 1797, 1675 cm$^{-1}$, NMR (DMSO-d$_6$): 1.4 (s,3H), 1.5 (s,3H), 1.7–2.1 (m,4H), 2.3–2.5 (m,1H), 3.0–3.9 (m,9H), 4.9 (s,1H), 5.1 (m,1H), 5.3–5.7 (m,2H), 6.9 (bs,1H,D$_2$O exchangeable) and 7.3 (bs,1H,D$_2$O exchangeable) ppm). |

EXAMPLE 3

The procedure of Example 1 was repeated with the same starting materials except that chloroform rather than tetrahydrofuran was the solvent and amines other than 3,5-lutidine were employed. The starting amines and the resulting products are tabulated in Table 2.

TABLE 2

| Amines | Product |
|---|---|
| 4-N,N—dimethylamino-pyridine | 1-(4',4'-dioxo-penicillanoyloxymethyl)-4-N,N—dimethylaminopyridinium iodide, 71% yield, NMR (DMSO-d$_6$): 1.4 (s,3H), 1.5 (s,3H), 3.3 (s,6H), 3.1–3.9 (m,2H), 4.6 (s,1H), 5.1–5.3 (m,1H), 6.25 (s,2H), 7.0–7.2 (d, J = 7, 2H), 8.3–8.5 (d, J = 7, 2H) ppm) |
| 1-methylimidazole | 3-(4',4'-dioxo-penicillanoyloxymethyl)-1-methylimidazolium iodide (m.p. 183–84° C. (d) 88% yield, IR: 1806, 1761 cm$^{-1}$, NMR (DMSO-d$_6$): 1.4 (s,3H), 1.5(s,3H), 3.1–3.9 (m,2H), 3.95 (s,3H), 4.6 (s,1H), 5.1–5.3 (m,1H), 6.25 (s,2H), 7.7–8.0 (m,2H), 9.4 (s,1H) ppm). |

EXAMPLE 4

1-(4',4'-Dioxo-penicillanoyloxymethyl)-3-acetyl-pyridinium Iodide

To a solution of 1.0 g. (2.68 mmole) iodomethyl 4,4-dioxopenicillanate in 5 ml. tetrahydrofuran, 0.32 g (2.6 mmol) of 3-acetylpyridine was added while stirring at 25° C. Stirring was continued for 5 hours at which time 10 ml. of diethyl ether were added. A bright yellow precipitate formed which was isolated by filtration and dried in vacuo to give 0.44 g. of the yellow crystalline solid title product (yield ca. 33%), m.p. 176°–78° C. (d). The IR spectrum of the product (KBr disc) showed absorptions at 1802, 1766 and 1699 cm$^{-1}$. The NMR spectrum (DMSO-d$_6$) showed absorptions at 1.4 (s, 3H), 1.5 (s, 3H), 2.77 (s, 3H), 3.0–3.9 (m, 2H), 4.6 (s, 1H), 5.1–5.3 (m, 1H), 6.4–6.8 (m, 2H), 8.43 (d of d, J=6 and 7, 1H), 9.22 d, J=7, 1H), 9.45 (d, J=6, 1H) and 9.83 (s, 1H) ppm.

EXAMPLE 5

The procedure of Example 4 was repeated with the same starting materials except that amines other than 3-acetylpyridine were employed to obtain the corresponding 4,4-dioxopenicillanate product as tabulated in Table 3.

TABLE 3

| bicyclo[2.2.2]-1,4-diazaoctane | bicyclo[2.2.2]-1-(4',4'-dioxo-penicillanoyloxymethyl)-1,4-diazaoctanyl iodide (75% yield, IR: 1785 cm$^{-1}$, NMR(DMSO-d$_6$): 1.4(s,3H), 1.5(s,3H), 2.8–4.2 (m,14H), 5.0(s,1H), 5.2–5.4 |
|---|---|

TABLE 3-continued

| | (m,1H), 5.3–5.7(m,2H) ppm). |
|---|---|
| methyl nicotinate | 1-(4',4'-dioxopenicillanoyloxy-methyl)-3-carbonyloxymethyl-pyridinium iodide (m.p.: 150–152° C.(d), 46% yield, IR: 1802, 1774, 1738 cm$^{-1}$, NMR(DMSO-d$_6$): 1.4(s,3H), 1.5 (s,3H), 3.0–3.8(m,2H), 4.0 (s,3H), 4.6(s,1H), 5.1 (d of d, J = 2, H), 6.5–6.9 (m,2H), 8.3–8.7 (d of d, J = 6 and 7, 1H), 9.13(d, J = 7, 1H), 9.41 (d, J = 6, 1H), 9.83(bs,1H), ppm). |
| 4-acetylpyridine | 1-(4',4'-dioxopenicillanoyloxy-methyl)-4-acetyl-pyridinium iodide (m.p.: 154–156° C.(d), 36% yield, IR: 1803, 1761, 1705 cm$^{-1}$, NMR(DMSO-d$_6$): 1.4(s,3H), 1.5 (s,3H), 2.61(s,3H), 3.0–3.9 (m,2H), 4.6(s,1H), 5.1–5.3(m,1H), 8.67(d, J = 8, 2H), 9.5(d, J-8.2H) ppm). |
| 2,4,6-trimethylpyridine | 1-(4',4'-dioxopenicillanoyloxy-methyl)2,4,6-trimethyl-pyridinium iodide (m.p.: 159–60(d), 25% yield, IR: 1796, 1799 cm$^{-1}$, NMR(DMSO-d$_6$): 1.4(s,3H) 1.5 (s,3H), 2.5(s,6H), 2.61(s,3H), 3.1–3.9(m,2H), 4.6(s,1H), 5.1–5.3(m,1H), 6.6–6.8(m,2H), 9.3(b,2H) ppm.) |
| methyl isonicotinate | 1-(4',4'-dioxopenicillanoyloxy-methyl)-4-carbonylmethyl-pyridinium iodide (m.p.: 144° C.(d), 54% yield, IR: 1790, 1766, 1738 cm$^{-1}$, NMR(DMSO-d$_6$): 1.4(s,3H), 1.5(s,3H), 3.1–3.9 (m,2H), 4.01(s,3H), 4.6(s,1H), 5.1–5.3(m,1H), 6.5–6.9(m,2H), 8.5–8.7(d, J = 6,2H), 9.3–9.5 (d,J = 6,2H), ppm). |

EXAMPLE 6

1-(4',4'-Dioxopenicillanoyloxymethyl)-4-cyanopyridinium Iodide

The same procedure and starting materials as in Example 4 were employed except that the starting amine was 4-cyanopyridine rather than 3-acetylpyridine and the solvent was a mixture of tetrahydrofuran and acetonitrile in the volume-to-volume ratio of 5:0.2 rather than THF. The title product was obtained (0.2 g, 16% yield) having a melting point of 188° C. (d). The product had IR absorptions at 1791 and 1769 cm$^{-1}$. The NMR spectrum (DMSO-d$_6$) showed absorptions at 1,4 (s, 3H), 1.5 (s, 3H), 3.1–3.9 (m, 2H), 4.6 (s, 1H), 5.1–5.3 (m, 1H), 6.5–6.9 (m, 2H), 8.7–8.9 (d, J=7, 2H) and 9.5–9.7 (d, J=7, 2H) ppm.

EXAMPLE 7

1-(4',4'-Dioxopenicillanoyloxymethyl)-4-tert-butylpyridinium chloride

To a solution of 1.0 g (3.55 mmole) of chloromethyl 4,4-dioxopenicillanate in 5 ml of tetrahydrofuran, 0.46 g (3.4 mmole) of 4-tert-butylpyridine was added while stirring at 25° C. Stirring continued for 72 hours at 25° C. following addition. A precipitate was filtered, washed with tetrahydrofuran and dried in vacuo to give 0.74 g of a white solid which was a mixture of the titled product and unreacted chloromethyl ester. The white solid was suspended in 20 ml of an ice-H$_2$O mixture, stirred vigorously and filtered. The aqueous filtrate was washed with methylene chloride and freeze dried to give 0.25 g of the titled compound as a white solid. The NMR spectrum (DMSO-d$_6$) showed absorptions at 1.4 (s, 12H), 1.5 (s, 3H), 3.0–3.8 (m, 2H), 4.6 (s, 1H), 4.8–5.3 (m, 1H), 6.5 (s, 2H), 8.1–8.3 (d, J=7 Hz, 2H) and 9.1–9.3 (d, J=7 Hz, 2H) ppm.

EXAMPLE 8

The bioassay procedure with out-bred Sprague-Dawley rats previously described was employed on the 4,4-dioxopenicillanate products of Example 1–7. All of the products were soluble in the diluent at the dose employed. All of the products when orally administered to the rats yielded blood serums containing 4,4-dioxopenicillanic acid.

PREPARATION A

Chloromethyl 4,4-Dioxopenicillanate

A mixture of 4.66 g of 4,4-dioxopenicillanic acid, 50 ml of dichloromethane and 35 ml of water was treated with sufficient tetrabutylammonium hydroxide (40% in water) to give a pH of 6.0. The dichloromethane layer was separated and the aqueous phase extracted with fresh dichloromethane (2×50 ml). The organic layers were combined, dried over sodium sulfate and concentrated to give 10.1 g of the tetrabutylammonium salt of 4,4-dioxopenicillanic acid.

The tetrabutylammonium 4,4-dioxopenicillanate product was added to 50 ml of chloroiodomethane and the reaction mixture was allowed to stir at ambient temperature overnight. The reaction mixture was concentrated to half volume in vacuo, and chromatographed on 200 g of silica gel using ethyl acetate/hexane as the eluant, 12 ml cuts being taken every 30 sec. Fractions 41–73 were combined and concentrated to dryness to give 3.2 g of the title compound.

The NMR spectrum (CDCl$_3$) showed absorptions at 1.5 (s, 3H), 1.66 (s, 3H) 3.43 (d, 2H), 4.38 (s, 1H), 4.6 (t, 1H) and 5.7 (d of d, 2H) ppm.

PREPARATION B

Iodomethyl 4,4-Dioxopenicillanate

To a solution of 7.9 g of chloromethyl 4,4-dioxopenicillanate in 100 ml of dry acetone maintained under a nitrogen atmosphere was added 21.0 g of sodium iodide, and the reaction mixture was allowed to stir overnight at room temperature. The reaction mixture was concentrated in vacuo, and the residue was dissolved in 150 ml. ethyl acetate and 150 ml water. The organic layer was separated and the aqueous layer was extracted with fresh ethyl acetate. The organic extracts were combined with the organic layer, washed with water (1×500 ml) and brine (1×50 ml.) and dried over sodium sulfate. Removal of the solvent gave 10.5 g of the title product, m.p. 100°–102° C.

The NMR spectrum (CDCl$_3$) showed absorptions at 1.55 (s, 3H), 1.68 (s, 3H), 3.5 (d, 2H), 4.4 (s, 1H), 4.65 (t, 1H) and 6.0 (d of d, 2H) ppm.

I claim:

1. A compound of the formula

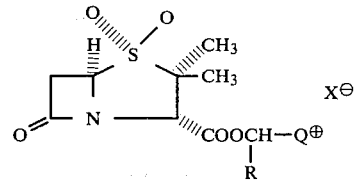

wherein:

R is hydrogen;

Q is chosen so that the compound hydrolyzes in vivo to 4.4-dioxopenicillanic and is selected from the group consisting of N(R$_1$) (R$_2$) (R$_3$) wherein R$_1$, R$_2$ and R$_3$ are each alkyl having 1–4 carbon atoms, hydroxyalkyl having 1–4 carbon atoms, alkoxycarbonylalkyl wherein the alkyl has 1–4 carbon atoms and the alkoxy has 1–4 carbon atoms or aminocarbonylalkyl wherein the alkyl has 1–4 carbon atoms, N-alkyl-morpholyl wherein the alkyl has 1–4 carbon atoms, N-alkyl-piperidyl wherein the alkyl has 1–4 carbon atoms or N-alkyl-pyrrolidyl wherein the alkyl has 1–4 carbon atom, and those groups substituted at a ring position with alkyl having 1–4 carbon atoms, aminocarbonyl, hydroxyl or alkoxycarbonyl wherein the alkoxy has 1–4 carbon atoms, bicyclo [2.2.2]1-,4-diazaoctanyl and those substituted with alkyl having 1–4 carbon atoms, aminocarbonyl, hydroxyl or alkoxycarbonyl wherein the alkoxy has 1–4 carbon atoms, pyridyl, alkylpyridyl wherein the alkyl has 1–4 carbon atoms, dialkylpyridyl wherein each alkyl has 1–4 carbon atoms, trialkylpyridyl wherein each alkyl has 1–4 carbon atoms, halopyridyl, cyanopyridyl, nitropyridyl, aminocarbonylpyridyl, N-alkylaminocarbonylpyridyl wherein the alkyl has 1–4 carbon atoms, N,N-dialkylaminocarbonylpyridyl wherein each alkyl has 1–4 carbon atoms, alkoxycarbonylpyridyl wherein the alkoxy contains 1–4 carbon atoms, or N,N-dialkylaminopyridyl wherein each alkyl has 1–4 carbon atoms, and quinolyl or N-alkylimidazolyl wherein the alkyl has 1–4 carbon atoms; and X$^-$ is a pharmaceutically-acceptable anion.

2. A compound according to claim 1 wherein Q is 4-methylpyridyl, 4-t-butylpyridyl, 4-cyanopyridyl, 4-N,N-dimethylaminopyridyl, 4-acetylpyridyl, isonicotinamidyl, methyl isonicotinatyl, 3-chloropyridyl, 3-acetylpyridyl, nicotinamidyl, methyl nicotinatyl, 3,5-lutidyl, 2,4,6-trimethylpyridyl, 1-methyl-3-imidazolyl, N-methylmorpholyl, N-methylpiperidyl, N-methylpyrrolidyl, 4-aminocarbonyl-N-methylpiperidyl, quinolyl or bicyclo [2.2.2]-1,4-diazaoctanyl.

3. A compound according to claim 1 wherein X$^-$ is chloride, bromide or iodide.

4. A pharmaceutical composition useful for treating infections in mammals which comprises a penicillin, or pharmaceutically acceptable salt thereof, and a compound of claim 1.

5. A pharmaceutical composition useful for treating infections in mammals which comprises a cephalosporin, or a pharmaceutically acceptable salt thereof, and a compound of claim 1.

6. A pharmaceutical composition according to claim 4 wherein the penicillin is:
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)penicillanic acid,
6-(D-2-amino-2-[1,4-cyclohexadienyl]acetamido)penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-[3-methylsulfonylimidazolin-2-one-1-carboxamido]-2-phenylacetamido)penicillanic acid,
6-([hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)penicillanate,
6-(2-phenxoycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)penicillanic acid,
6-(2-phenoxycarbonyl-2-[3-thienyl]acetamido)penicillanic acid,
6-(2-tolyloxycarbonyl-2-[3-thienyl]acetamido)penicillanic acid,
6-(2-[5-indanyloxycarbonyl]-2-[3-thienyl]acetamido)penicillanic acid, or
6-(2,2-dimethyl-5-oxo-4-phenyl-1-imidazolidinyl)penicillanic acid, and
the pharmaceutically acceptable salts thereof.

7. A pharmaceutical composition according to claim 5 wherein the cephalosporin is:
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-amino-2-phenylacetamido)-3-desacetoxycephalosporanic acid,
7-(D-2-phenylglycinamido)-3-chloro-3-desacetoxymethylcephalosporanic acid,
7-(D-2-[4-ethylpiperazin-2,3-dione-1-carboxamido]-2-[4-hydroxyphenyl]-acetamido)-3-([1-methyl-5-tetrazolyl]thiomethyl)-3-desacetoxymethylcephalosporanic acid,
7-(2-cyanoacetamido)cephalosporanic acid,
7-(2-[4-pyridylthio]acetamido)cephalosporanic acid,
7-(D-2-hydroxy-2-phenylacetamido)-3-([1-methyl-5-tetrazolyl]thiomethyl)-3-desacetoxymethylcephalosporanic acid,
7-(D-2-amino-2-[1,4-cyclohexadienyl]acetamido)cephalosporanic acid, or
7-(D-2-amino-2-phenylacetamido)cephalosporanic acid, and the pharmaceutically acceptable salts thereof.

8. A method of treating an infection in a mammal which comprises administering to the mammal a beta-lactam antibiotic, or a pharmaceutically acceptable salt thereof, and a compound of claim 1 wherein the antibiotic is a penicillin or a cephalosporin.

9. A method according to claim 8 wherein the antibiotic is a penicillin.

10. A method according to claim 8 wherein both the antibiotic and the compound are administered orally.

11. A method according to claim 8 wherein the compound is administered orally and the antibiotic is administered parenterally.

12. A method according to claim 8 wherein the antibiotic is a cephalosporin.

13. A compound according to claim 2, wherein Q is 4-aminocarbonyl-N-methyl-piperidyl.

* * * * *